(12) United States Patent
Shemesh

(10) Patent No.: US 6,648,835 B1
(45) Date of Patent: Nov. 18, 2003

(54) FLUID SAMPLING APPARATUS

(75) Inventor: Eli Shemesh, Ashdod (IL)

(73) Assignee: Teva Medical Ltd., Ashdod (IL)

( * ) Notice: Subject to any disclaimer, the term of this patent is extended or adjusted under 35 U.S.C. 154(b) by 0 days.

(21) Appl. No.: 09/913,677

(22) PCT Filed: Dec. 23, 1999

(86) PCT No.: PCT/IL99/00700

§ 371 (c)(1),
(2), (4) Date: Dec. 7, 2001

(87) PCT Pub. No.: WO00/49939

PCT Pub. Date: Aug. 31, 2000

(30) Foreign Application Priority Data

Feb. 24, 1999 (IL) ................................................. 128709

(51) Int. Cl.⁷ ................................................. A61B 5/00
(52) U.S. Cl. ........................ 600/573; 600/576; 600/577
(58) Field of Search ............................... 600/576, 577, 600/578, 573, 583; 604/412, 413, 414

(56) References Cited

U.S. PATENT DOCUMENTS

| 3,841,835 A | 10/1974 | Kishimoto et al. ....... 23/253 R |
| 3,877,465 A | 4/1975 | Miyake ..................... 128/2 F |
| 4,266,543 A | 5/1981 | Blum ..................... 128/218 N |
| 4,843,017 A | 6/1989 | Oberhardt et al. ........... 436/177 |
| 4,935,012 A | * 6/1990 | Magre et al. ................ 604/192 |
| 5,084,034 A | 1/1992 | Zanotti ...................... 604/319 |
| 5,125,414 A | 6/1992 | Dysarz ....................... 128/763 |
| 5,360,012 A | 11/1994 | Ebara et al. ................. 128/764 |
| 5,429,612 A | * 7/1995 | Berthier ...................... 604/198 |
| 5,456,678 A | 10/1995 | Nicoletti .................... 604/413 |
| 5,620,008 A | 4/1997 | Shinar et al. ............... 128/764 |
| 5,658,271 A | 8/1997 | Loubser ..................... 604/410 |
| 6,123,859 A | 9/2000 | Lee et al. ................... 210/767 |

FOREIGN PATENT DOCUMENTS

| EP | 0329660 | 8/1989 |
| WO | 88/01846 | 3/1988 |
| WO | WO 97/45714 | 12/1997 |

* cited by examiner

Primary Examiner—Max F. Hindenburg
Assistant Examiner—Jonathan Foreman
(74) Attorney, Agent, or Firm—Ladas & Parry

(57) ABSTRACT

A fluid sampling apparatus including an elongate housing, a needle mount slidingly mounted in the elongate housing, a double-pointed needle adapted for flow of fluid therethrough, the needle being fixedly mounted in the needle mount with a proximal point extending proximally outwards of the needle mount and a distal point extending distally outwards of the needle mount, a seal plug mounted in the distal portion of the housing, the seal plug being aligned with the needle such that the distal point can pierce through the seal plug into a puncturable conduit and a biasing device positioned between the seal plug and a distal face of the needle mount and a flexible ring mounted in the housing operative to reversibly grip a head of a vacuum tube inserted through a proximal end of the housing.

15 Claims, 3 Drawing Sheets

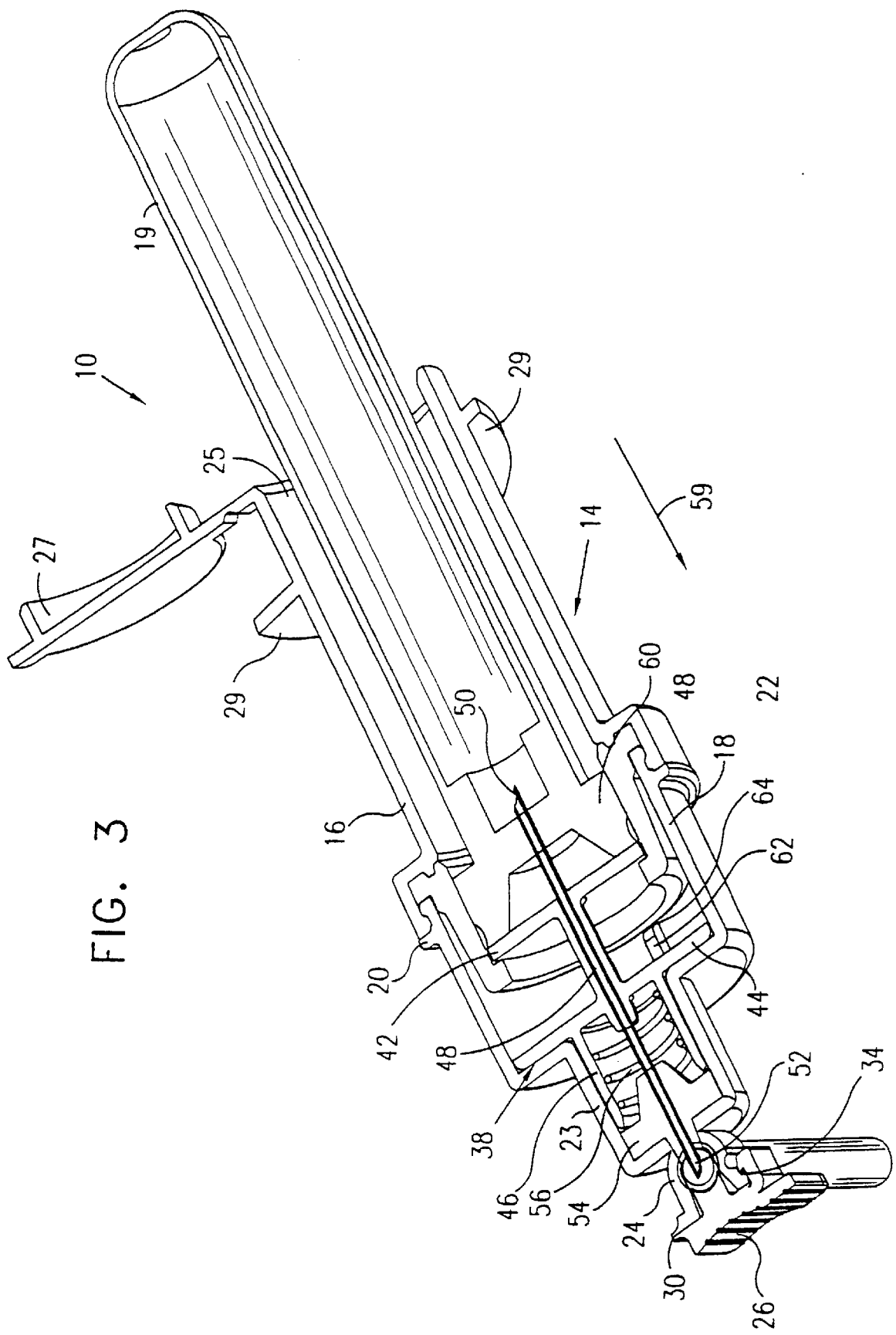

FLUID SAMPLING APPARATUS

FIELD OF THE INVENTION

The present invention relates to fluid sampling apparatus generally, and particularly to apparatus for sampling blood from a puncturable conduit.

BACKGROUND OF THE INVENTION

Various types of apparatus for sampling fluids are known. In particular, various types of blood sampling devices are known in the art. The following patent documents are believed to represent the most relevant prior art: U.S. Pat. No. 3,841,835 to Kishimoto et al., U.S. Pat. No. 3,877,465 to Miyake, U.S. Pat. No. 4,266,543 to Blum, U.S. Pat. No. 4,843,017 to Oberhardt et al., and U.S. Pat. No. 5,360,012 to Ebara et al., and PCT Published Patent Application WO 97/45714, which is assigned to the present assignee.

A problem with current blood sampling devices is that they incorporate a latex sheath-covered needle. The latex recedes to the bottom of the needle during blood sampling with a vacuum tube, thus exposing the needle point. It retracts to cover the needle when the sampling tube is withdrawn, thus preventing blood from leaking out of the needle. As latex sheaths are not robust articles, they will often fail to retract, resulting in donor blood leakage. It would be desirable, therefore, to have a blood sampling apparatus in which the need for a needle cover sheath is obviated.

A problem also exists in donation of blood for which the prior art has no known convenient and economical solution. Often when blood is drawn from a donor the very first amount of blood may have bacterial contamination, for example, due to bacteria or other germs found on the skin of the donor which can enter the blood upon puncturing the skin. Accordingly, it would be desirable to separate this first quantity of blood from the blood collected in a donor bag. In many prior art sampling systems, a permanent disturbance (such as a needle tip) is introduced into the blood stream, causing turbulence and coagulation. Therefore, they are suitable only for sampling after donation and not for first blood collection.

SUMMARY OF THE INVENTION

The present invention seeks to provide novel and easy-to-use blood sampling apparatus for use with puncturable conduits, and which solves the abovementioned problems. In the present invention, a blood donor is attached to conventional blood donation apparatus including a blood conduit which leads drawn blood into a sterile blood bag. The sampling apparatus of the present invention is attached to the blood donation apparatus and permits, if desired, selectively diverting an initial, small quantity of blood at the beginning of blood donation into a sealed vacuum tube. This initial quantity which can contain bacterial contamination is thus diverted from the main collected blood volume. It is a particular feature of the present invention that the sampling apparatus diverts the flow of blood from the blood conduit without disturbing the continuity of blood flow towards the donor bag. Any number of vacuum tube samplings can be drawn with the present invention, and, of course, the blood can be drawn into the vacuum tube at any time other than that of the initial quantity.

In one preferred embodiment of the present invention, a vacuum tube is brought into puncturing engagement with the blood conduit by pushing the vacuum tube against a spring in the sampling apparatus. A flexible, elastomeric ring fixedly grips the head of the vacuum tube during drawing of blood thereinto. The sampling apparatus preferably contains no latex and includes embodiments which can be sterilized either with steam or ethylene oxide (ETO).

There is thus provided in accordance with a preferred embodiment of the present invention fluid sampling apparatus including an elongate housing including a conduit puncturing portion at a distal end thereof, the conduit puncturing portion being adapted to receive therein a puncturable conduit, a needle mount slidingly mounted in the elongate housing, a double-pointed needle adapted for flow of fluid therethrough, the needle being fixedly mounted in the needle mount with a proximal point extending proximally outwards of the needle mount and a distal point extending distally outwards of the needle mount, a seal plug mounted in the distal portion of the housing, the seal plug being aligned with the needle such that the distal point can pierce through the seal plug into a puncturable conduit, and a biasing device positioned between the seal plug and a distal face of the needle mount, the biasing device having a first position wherein the distal face of the needle mount is spaced from the seal plug and the distal point of the needle does not distally protrude through the seal plug, and the biasing device having a second position wherein the needle mount is slid distally and the distal point distally protrudes through the seal plug and can pierce a puncturable conduit received in the conduit puncturing portion.

In accordance with a preferred embodiment of the present invention in the first position the biasing device is in a non-compressed state, and in the second position the biasing device is in a compressed state. Preferably the biasing device includes a spring.

Further in accordance with a preferred embodiment of the present invention a clamp extends from the conduit puncturing portion.

Still further in accordance with a preferred embodiment of the present invention the needle mount includes a disc radially extending therefrom and the housing includes a distal shoulder against which the disc can abut in the second position.

Additionally in accordance with a preferred embodiment of the present invention a flexible ring is mounted in the housing operative to grip a head of a vacuum tube inserted through a proximal end of the housing. The disc of the needle mount can proximally slidingly abut against the flexible ring.

In accordance with a preferred embodiment of the present invention the housing includes two portions attached together and sealed by the flexible ring.

Further in accordance with a preferred embodiment of the present invention the needle mount is slidingly mounted in the elongate housing by means of a tongue-and-groove slider which substantially prevents rotation of the needle about its longitudinal axis.

Still further in accordance with a preferred embodiment of the present invention a proximal end of the housing is sealed by a cap. The cap may be integrally formed with the housing.

Additionally in accordance with a preferred embodiment of the present invention one or more tabs radially extend from an outside surface of the housing.

In accordance with a preferred embodiment of the present invention the fluid sampling apparatus is autoclavable.

BRIEF DESCRIPTION OF THE DRAWINGS

The present invention will be understood and appreciated more fully from the following detailed description, taken in conjunction with the drawings in which:

FIGS. 2 and 3 are simplified sectional illustrations of the fluid sampling apparatus of FIG. 1, before and after puncturing a puncturable conduit, respectively.

DETAILED DESCRIPTION OF A PREFERRED EMBODIMENT

Figure 1:
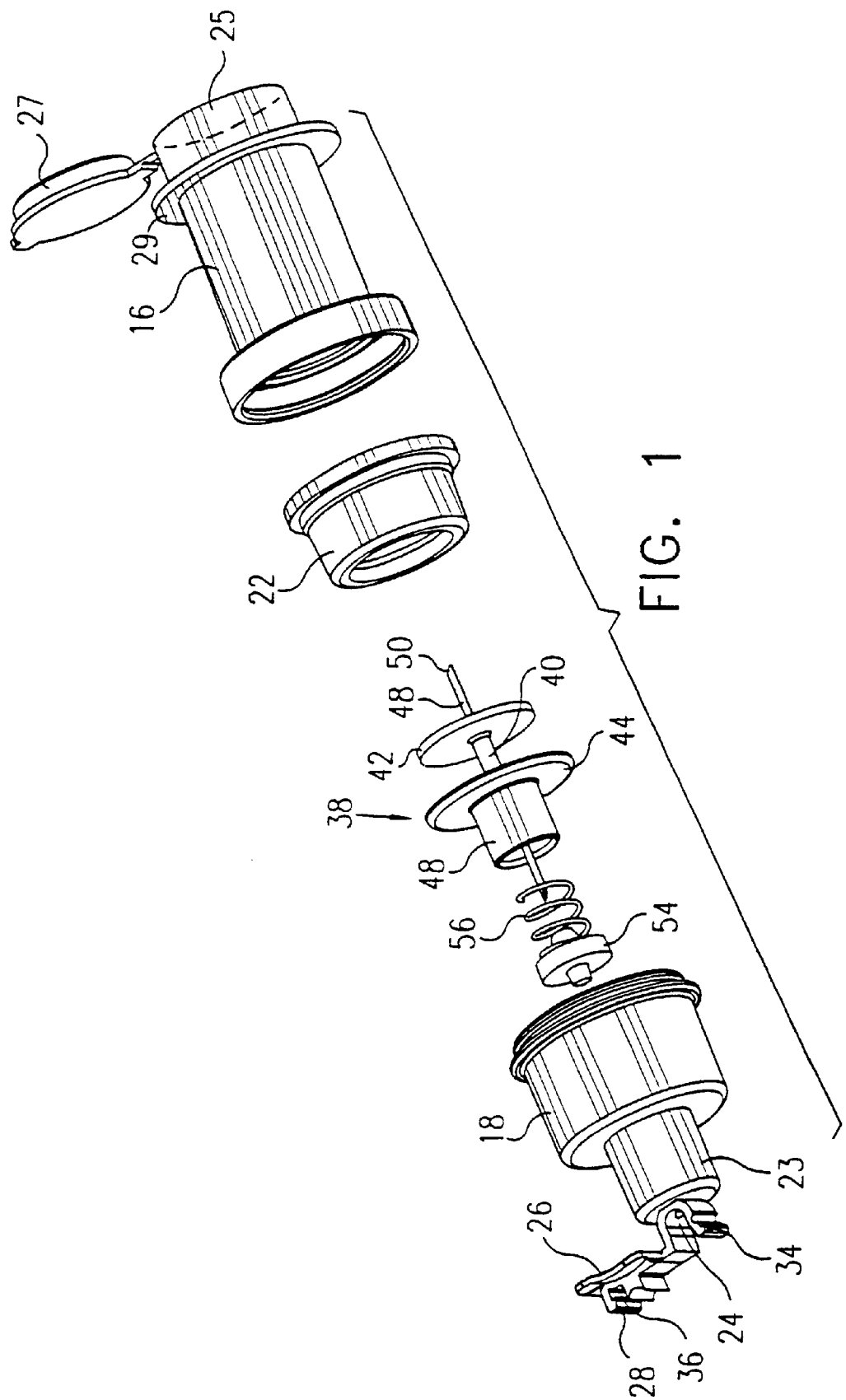
FIG. 1 is a simplified, exploded pictorial illustration of fluid sampling apparatus, constructed and operative in accordance with a preferred embodiment of the present invention.
Figure 2:
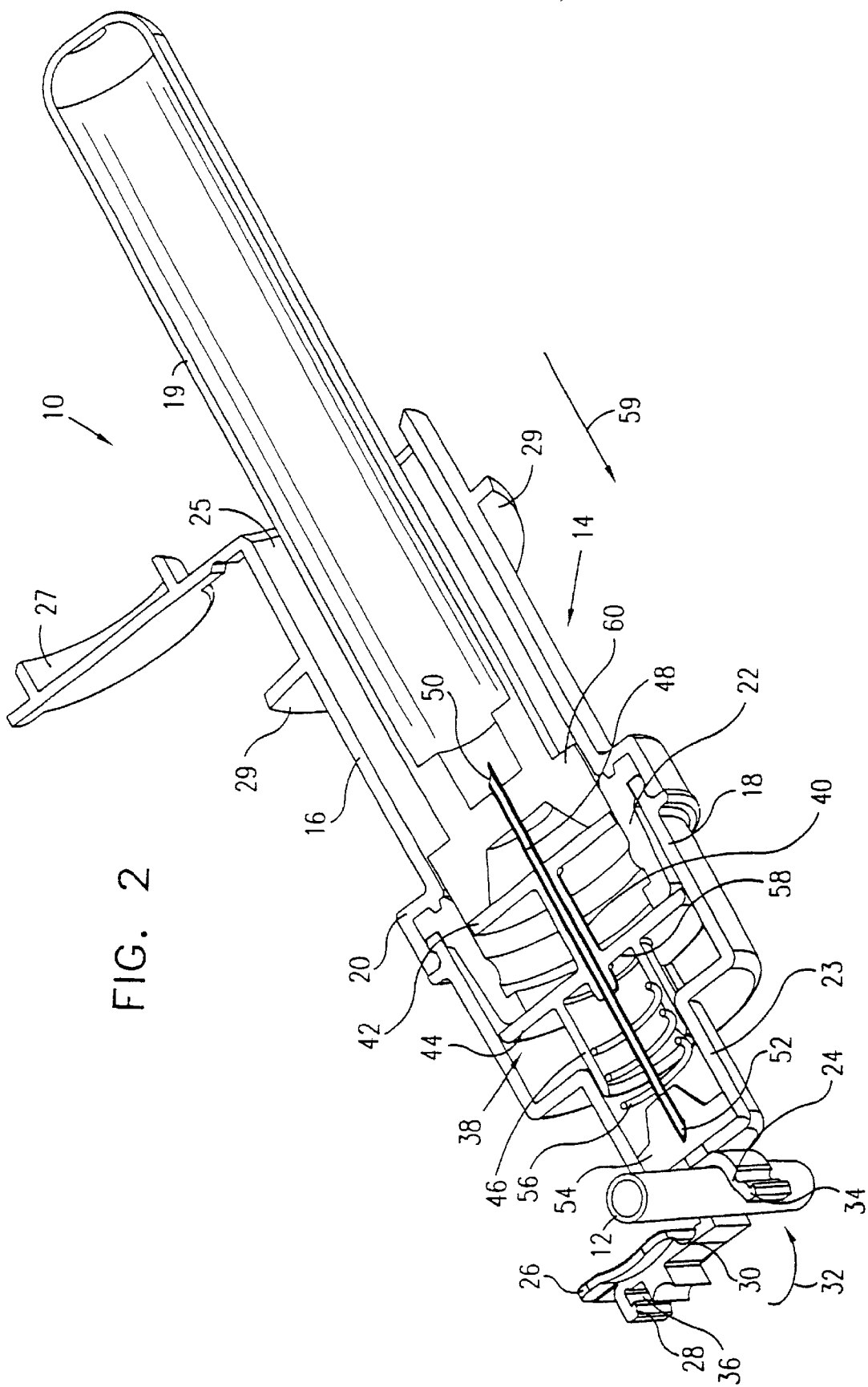

Reference is now made to FIGS. 1–3 which illustrate fluid sampling apparatus 10, constructed and operative in accordance with a preferred embodiment of the present invention, and which can be used to puncture a puncturable conduit 12. Apparatus 10 is particularly useful in applications such as, donation of blood. In such a case, conduit 12 would be a blood donor tube attached to a blood donor, and apparatus 10 would be used to collect blood therefrom, as will be described further hereinbelow.

Apparatus 10 preferably includes an elongate housing 14, typically formed of plastic by injection molding. Housing 14 preferably comprises a generally circular cylindrical portion 16 and a neck portion 18 which are joined at a shoulder 20 formed on portion 16. Portion 16 is preferably longer and of smaller radius than neck portion 18, portion 16 being intended for operative engagement with a vacuum tube 19 (not shown in FIG. 1). Portion 16 and neck portion 18 may be constructed separately and joined in any convenient manner such as by snapping or bonding together. The two portions may be sealed relative to each other by means of a flexible ring 22 which acts as an O-ring at the Juncture of portions 16 and 18. Flexible ring 22 is preferably constructed of an elastomer, such as a medically safe synthetic rubber.

Neck portion 18 preferably includes a distally extending narrow portion 23 which terminates in an outwardly extending conduit puncturing portion 24. As seen in FIGS. 2 and 3, conduit puncturing portion 24 is adapted to receive therein conduit 12. Preferably hingedly attached to conduit puncturing portion 24 is a clamp 26. Clamp 26 preferably has an engagement cutout portion 28 formed therein and includes a relatively thin pivoting portion 30. By folding clamp 26 in the direction of an arrow 32 (FIG. 2) about pivoting portion 30, a flange 34, preferably located at an extreme end of conduit puncturing portion 24, snappingly engages with engagement cutout portion 28, as shown in FIG. 3. Clamp 26 preferably further includes a conduit interface element 36 which is substantially shaped complementarily to the outer periphery of conduit 12.

A proximal end 25 of portion 16 of housing 14 is preferably open and may be sealed by a cap 27. Cap 27 may be integrally formed with housing 14 or alternatively may be supplied separately. Cap 27 may include a push-on type of cap which snugly and sealingly fits onto proximal end 25, or alternatively may be a membrane secured to end 25 by bonding or welding, for example. Such a membrane may be rupturable when pushed against by vacuum tube 19.

One or more tabs 29 preferably radially extend from an outside surface of housing 14. Tabs 29 are useful in grasping housing 14 during distal pushing of vacuum tube 19, as is described further hereinbelow.

A needle mount 38 is preferably slidingly mounted in neck portion 18 of housing 14. Needle mount 38 preferably includes a hollow tube 40 from which radially extend a proximal disc 42 and a distal disc 44. The two discs are preferably spaced from each other, and distal disc 44 is preferably larger in diameter than proximal disc 42. A hollow hub 46 extends distally from distal disc 44. Distal disc 44 is sized to slide within neck portion 18 and hub 46 is sized to slide in narrow portion 23.

A double-pointed needle 48 is fixedly mounted in tube 40 of needle mount 38 with a proximal point 50 extending proximally outwards of needle mount 38 and a distal point 52 extending distally outwards of needle mount 38. Needle 48 is hollow for flow of fluid therethrough. It is seen that elongate housing 14 is configured to substantially prevent inadvertent engagement of a user's finger with needle 48.

A seal plug 54 is preferably mounted in the distal portion of narrow portion 23 of housing 14. Seal plug 54 is aligned with needle 48 such that distal point 52 can pierce through seal plug 54 into conduit 12, as will be described further hereinbelow. Seal plug 54 substantially prevents leakage from a punctured conduit 12.

A biasing device 56, such as a coil spring made, for example, of a medical grade of stainless steel, is preferably positioned between seal plug 54 and a distal face 58 of needle mount 38. In a first position shown in FIG. 2, biasing device 56 is not compressed and spaces the distal face 58 of needle mount 38 from seal plug 54. In the first position, distal point 52 of needle 48 partially pierces seal plug 54 but does not distally protrude through plug 54. Thus needle 48 does not communicate with conduit 12 in the first position, and a fluid, such as blood, can flow through conduit 12 without being sampled by apparatus 10.

In order to sample a fluid, such as blood, from conduit 12. cap 27 is removed and vacuum tube 19 is introduced into housing 14 through proximal end 25. Preferably vacuum tube 19 is substantially hermetically sealed by a sealed head 60 which is punctured by proximal point 50 of needle 48 when vacuum tube 19 is pushed distally in housing 14 in the direction of an arrow 59 (FIGS. 2 and 3). The distally directed pushing of vacuum tube 19 causes head 60 to abut against disc 42 of needle mount 38. Further distal pushing of vacuum tube 19 compresses biasing device 56 and pushes distal point 52 of needle 48 through seal plug 54 so that distal point 52 punctures conduit 12, as seen in FIG. 3. In this position, called a second position, a portion of fluid such as blood, flowing in conduit 12 flows through needle 48 into vacuum tube 19, while the rest of the fluid continues to flow in conduit 12.

For convenience, tabs 29 can be gripped by the fingers of a phlebotomist using apparatus 10 when distally pushing vacuum tube 19 in housing 14.

In order that a phlebotomist does not have to constantly press vacuum tube 19 against the force of biasing device 56, flexible ring 22 is preferably configured to be of such shape and strength to grip head 60 of vacuum tube 19 when vacuum tube 19 is pushed thereinto. Flexible ring 22 can be whole or slitted longitudinally, for example. Flexible ring 22 holds vacuum tube 19 in place during flow of a fluid thereinto.

It is noted that disc 44 of needle mount 38 is limited in its sliding travel distally by a shoulder of narrow portion 23 and proximally by flexible ring 22.

Distal point 52 of needle 48 is generally chamfered as is known in the art, and it is important that the orientation of the chamfered point with respect to conduit 12 be maintained. In order to achieve this, structure is provided which substantially prevents rotation of needle 48 about its longitudinal axis. In a preferred embodiment of the present invention, this structure includes a tongue-and-groove slider, seen in FIG. 3. For example, a tongue 62 may be formed on neck portion 18 which engages and slides in a groove 64 formed in an underside of hub 46.

Upon completion of the blood sampling, vacuum tube 19 is removed from housing 14 of apparatus 10. Biasing device 56 then pushes needle mount 38 proximally, thus removing distal point 52 of needle 48 from conduit 12 and positioning it inside seal plug 54 (the position shown in FIG. 2), thereby preventing leakage from conduit 12 and needle 48.

In accordance with a preferred embodiment of the present invention, all parts of apparatus 10 are constructed of materials that can be sterilized by autoclaving. In one preferred embodiment, apparatus 10 may be sterilized with ethylene oxide (ETO). In such an embodiment, apparatus 10 may be supplied in a sterile bag without cap 27, and is attached to the donor tube by the phlebotomist. In another preferred embodiment, apparatus 10 may be sterilized by autoclaving in steam. In such an embodiment, apparatus 10 is preferably supplied with cap 27 sealingly affixed to proximal end 25 of housing 14 and with conduit 12 attached to conduit puncturing portion 24. Apparatus 10 is not packaged in a separate bag, and is sterilized by steam together with the blood bag system to which it is attached.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. Fluid sampling apparatus comprising:
    an elongate housing;
    a needle mount slidingly mounted in said elongate housing;
    a double-pointed needle adapted for flow of fluid therethrough, said needle being fixedly mounted in said needle mount with a proximal point extending proximally outwards of said needle mount and a distal point extending distally outwards of said needle mount;
    a seal plug mounted in said distal portion of said housing, said seal plug being aligned with said needle such that said distal point can pierce through said seal plug into a puncturable conduit;
    a biasing device positioned between said seal plug and a distal face of said needle mount, said biasing device having a first position wherein said distal face of said needle mount is spaced from said seal plug and said distal point of said needle does not distally protrude through said seal plug, and said biasing device having a second position wherein said needle mount is slid distally and said distal point distally protrudes through said seal plug; and can pierce a puncturable conduit; and
    a flexible ring mounted in said housing operative to reversibly grip a head of a vacuum tube inserted through a proximal end of said housing.

2. Fluid sampling apparatus according to claim 1 wherein in said first position said biasing device is in a non-compressed state, and in said second position said biasing device is in a compressed state.

3. Fluid sampling apparatus according to claim 1 wherein said biasing device comprises a spring.

4. Fluid sampling apparatus according to claim 1 further comprising a conduit puncturing portion at a distal portion of said housing, said conduit puncturing portion being adapted to receive therein a puncturable conduit.

5. Fluid sampling apparatus according to claim 4 further comprising a clamp extending from said conduit puncturing portion.

6. Fluid sampling apparatus according to claim 1 further comprising a puncturable conduit fixedly received in said conduit puncturing portion.

7. Fluid sampling apparatus according to claim 1 wherein said needle mount comprises a disc radially extending therefrom and said housing comprises a distal shoulder against which said disc can abut in said second position.

8. Fluid sampling apparatus according to claim 1 wherein said housing comprises two portions attached together and sealed by said flexible ring.

9. Fluid sampling apparatus according to claim 1 wherein said needle mount is slidingly mounted in said elongate housing by means of a tongue-and-groove slider which substantially prevents rotation of said needle about its longitudinal axis.

10. Fluid sampling apparatus according to claim 1 wherein a proximal end of said housing is sealed by a cap.

11. Fluid sampling apparatus according to claim 1 wherein said cap is integrally formed with said housing.

12. Fluid sampling apparatus according to claim 1 further comprising at least one tab radially extending from an outside surface of said housing.

13. Fluid sampling apparatus according to claim 1 wherein said fluid sampling apparatus is autoclavable.

14. Fluid sampling apparatus comprising:
    an elongate housing;
    a needle mount, slidingly mounted in said elongate housing;
    a double-pointed needle adapted for flow of fluid therethrough, said needle being fixedly mounted in said needle mount with a proximal point extending proximally outwards of said needle mount and a distal point extending distally outwards of said needle mount;
    a seal plug mounted in said distal portion of said housing, said seal plug being aligned with said needle such that said distal point can pierce through said seal plug into a puncturable conduit; and
    a biasing device positioned between said seal plug and a distal face of said needle mount, said biasing device having a first position wherein said distal face of said needle mount is spaced from said seal plug and said distal point of said needle does not distally protrude through said seal plug, and said biasing device having a second position wherein said needle mount is slid distally and said distal point distally protrudes through said seal plug and can pierce a puncturable conduit;
    said needle mount comprising a disc radially extending therefrom and said housing comprising a distal shoulder against which said disc can abut in said second position;
    said apparatus further comprising a flexible ring mounted in said housing; operative to reversibly grip a head of a vacuum tube inserted through a proximal end of said housing; and
    said flexible ring being, mounted proximally of said disc, wherein said disc of said needle mount can proximally slidingly abut against said flexible ring.

15. A method for drawing blood from a donor, characterized by:
    providing blood donation apparatus which includes a blood conduit fluidly connected to a blood donor bag;
    providing blood sampling apparatus fluidly connected to said blood conduit, said blood sampling apparatus comprising:

an elongate housing;

a needle mount slidingly mounted in said elongate housing;

a double-pointed needle adapted for flow of fluid therethrough, said needle being fixedly mounted in said needle mount with a proximal point extending proximally outwards of said needle mount and a distal point extending distally outwards of said needle mount;

a seal plug mounted in said distal portion of said housing, said seal plug being aligned with said needle such that said distal point can pierce through said seal plug into a puncturable conduit;

a biasing device positioned between said seal plug and a distal face of said needle mount, said biasing device having a first position wherein said distal face of said needle mount is spaced from said seal plug and said distal point of said needle does not distally protrude through said seal plug, and said biasing device having a second position wherein said needle mount is slid distally and said distal point distally protrudes through said seal plug and can pierce a puncturable conduit; and a flexible ring mounted in said housing operative to reversibly grip a head of a vacuum tube inserted through a proximal end of said housing;

drawing blood from a blood donor with the blood donation apparatus, wherein the blood flows through the blood conduit into the blood donor bag; and diverting a quantity of blood from the blood conduit into a vacuum tube which has a sealed head by the following steps:

inserting the vacuum tube into said elongate housing and pushing said vacuum tube distally so as to puncture said sealed head by said proximal point of said needle; and further distally pushing said vacuum tube so as to compress said biasing device and push said distal point of said needle through said seal plug so that said distal point punctures said blood conduit and blood flows through said needle into said vacuum tube.

* * * * *